Figure 5:
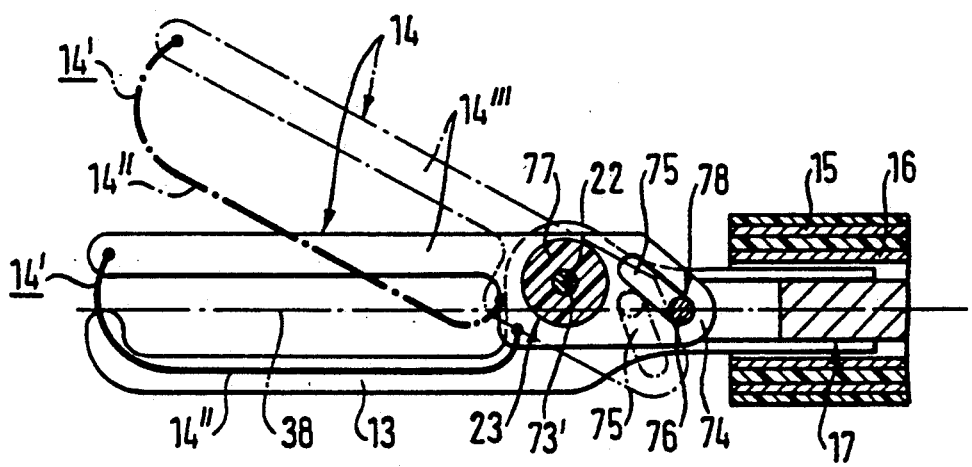

United States Patent [19]

Hagen

[11] Patent Number: 5,267,998
[45] Date of Patent: Dec. 7, 1993

[54] MEDICAL HIGH FREQUENCY COAGULATION CUTTING INSTRUMENT

[75] Inventor: Alfred Hagen, Tuttlingen, Fed. Rep. of Germany

[73] Assignee: Delma elektro-und medizinische Apparatebau Gesellschaft mbH, Tuttlingen, Fed. Rep. of Germany

[21] Appl. No.: 959,210

[22] Filed: Oct. 13, 1992

[30] Foreign Application Priority Data

Nov. 19, 1991 [DE] Fed. Rep. of Germany ....... 4138116

[51] Int. Cl.$^5$ ...................... A61B 17/36; A61B 17/39
[52] U.S. Cl. ........................................ 606/45; 606/46; 606/49; 606/50
[58] Field of Search ....................... 606/33, 34, 37, 41, 606/42, 45-52

[56] References Cited

U.S. PATENT DOCUMENTS 4,655,216 4/1987 Tischer ................. 606/51

FOREIGN PATENT DOCUMENTS 9206642 4/1992 World Int. Prop. O. ............ 606/45

Primary Examiner—Stephen C. Pellegrino
Assistant Examiner—Mike Peffley
Attorney, Agent, or Firm—Townsend and Townsend Khourie and Crew

[57] ABSTRACT

A medical coagulation-cutting instrument has an instrument shaft (11) with two stationary coagulation electrodes (12, 13) and a movable cutting electrode (14). An actuating head (19) is arranged at the distal end of the instrument shaft (11). The radio frequency feedlines for the two coagulation electrodes (12, 13) are conductive tubes (15, 16) arranged concentric to one another and to the instrument shaft within which the high frequency feedline for the cutting electrode (14) is arranged in an insulated manner as an axially directed conductive bar (17) which is axially movable by the actuating head (19).

16 Claims, 3 Drawing Sheets

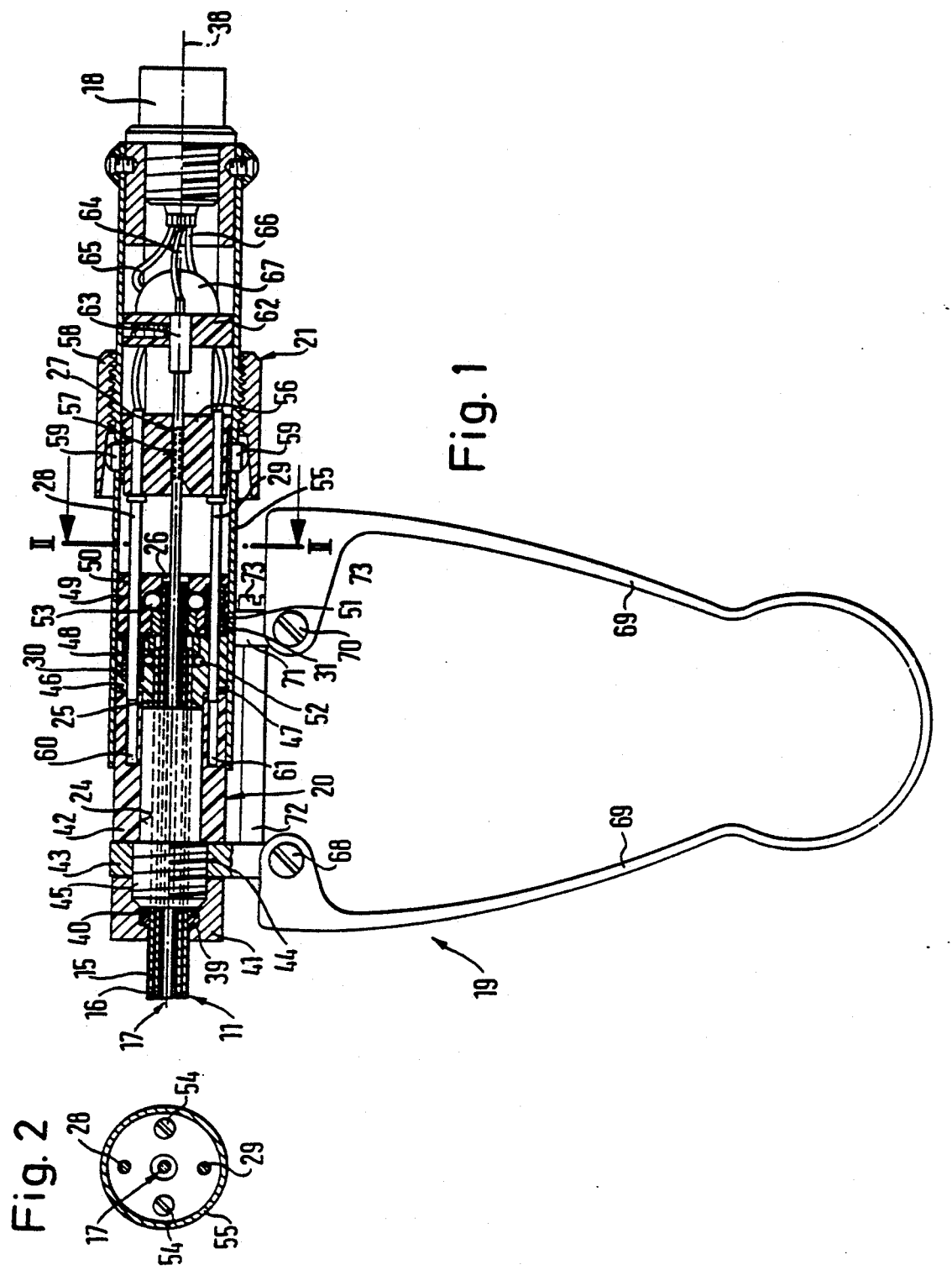

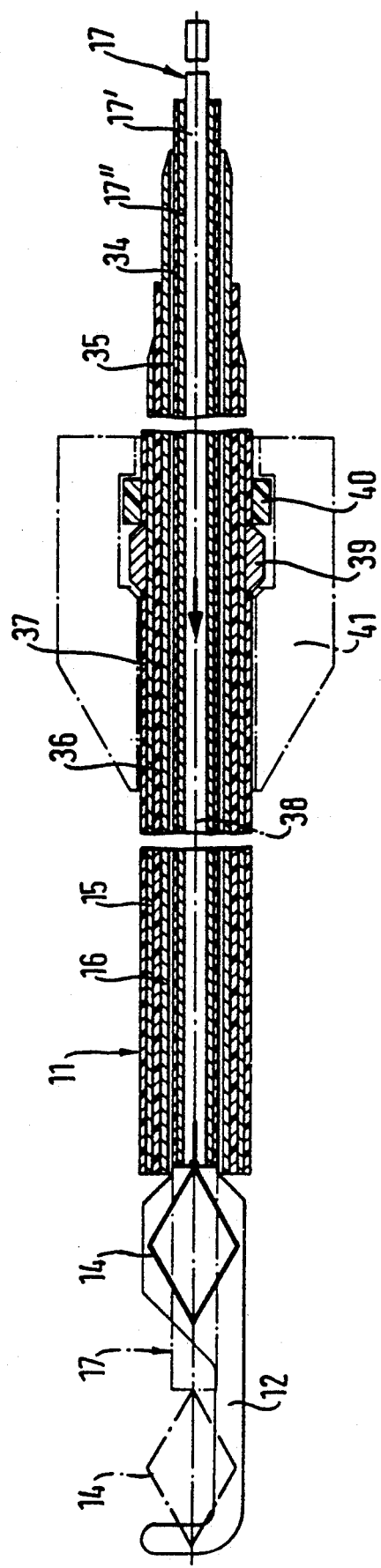
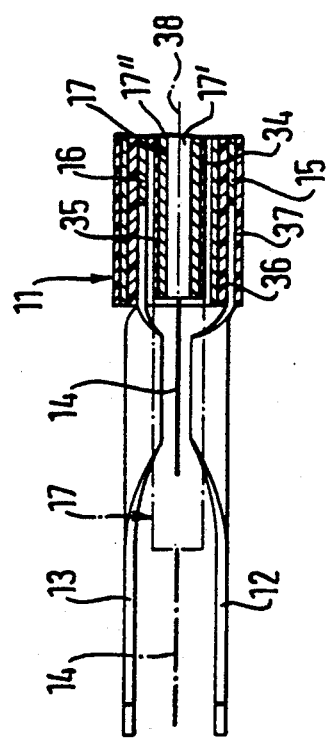
Fig. 3
Fig. 4

MEDICAL HIGH FREQUENCY COAGULATION CUTTING INSTRUMENT

DESCRIPTION

The invention relates to a medical radio frequency coagulation-cutting instrument comprising an instrument shaft at the proximal end of which there are provided two stationary coagulation electrodes and a movable cutting electrode; an actuating head arranged at the distal end of the instrument and consisting of a fixed head part and a head part which is movable relative thereto, wherein a relative movement of the two head parts is transmitted to the cutting electrode, wherein the coagulation electrodes and also the cutting electrode lead via radio frequency feedlines, which are led insulated relative to one another in the instrument shaft, to a cable connection which is preferably provided at the distal end for the purpose of connection to a radio frequency supply device, and wherein the radio frequency supply device has at least two switch positions, in one of which the cutting electrode is switched off and the coagulation electrodes are energised with a radio frequency coagulation current and in the other of which one or both of the coagulation electrodes are connected as neutral electrodes and a radio frequency voltage which enables a cutting arc is applied to the cutting electrode and the neutral electrode.

An instrument of this kind is known from the not prior published German Offenlegungsschrift 40 32 271. The two coagulation electrodes and the cutting electrode are axially non-displaceably arranged relative to one another in the instrument shaft. The cutting electrode is however pivotally arranged between the two coagulation electrodes disposed parallel to one another in as much as an outer guide tube can be axially displaced by means of the actuating head.

Furthermore, a pair of coagulation forceps is known (German Patent Specification 27 34 847) in which the two coagulation electrodes can be moved towards one another in forceps-like manner by advancing a rotor by means of the actuating head. A cutting electrode is not provided in this instrument.

Finally, it is known from the non-prior published German Offenlegungsschrift 41 22 219 to form two coagulation electrodes and their feed line as tubes which are arranged coaxially relative to one another and to arrange between them an axially displaceable cutting electrode which is supplied with radio frequency potential via a conductive bar arranged in an insulated manner within the tubes.

The object underlying the invention is to make available a further medical coagulation-cutting instrument. The coagulation-cutting instrument of the invention should in particular satisfy a whole variety of different coagulation and cutting tasks. It should also be easily dismantleable for the purpose of cleaning.

In order to satisfy this object there is provided, in accordance with the present invention, a medical radio frequency coagulation-cutting instrument of the initially named kind but characterised in that the radio frequency supply lines for the two coagulation electrodes are conductive tubes arranged within one another, preferably concentric to one another and to the instrument shaft, with the high frequency supply line for the cutting electrode being arranged inside the conductive tubes in an insulated manner as an axially directed conductive bar axially movable through the actuating head.

As a result of this construction a very stable design of the instrument shaft is ensured on the one hand, while on the other hand the radio frequency potentials and currents necessary to energise the coagulation electrodes and the cutting electrode can be supplied by means of a very compact and stable feedline arrangement. The cutting electrode is thereby supplied with a radio frequency potential suitable for cutting, with the two coagulation electrodes being connected together to form a neutral electrode. In the other switching state, the cutting electrode is retracted into the shaft of the instrument, or removed therefrom, and the two coagulation electrodes are then fed with a radio frequency coagulation current which brings about the desired heating on application of the two stationary coagulation electrodes to the tissue.

The axially movable conductive bar can be solid or can also be hollow and tubular or formed as an assembled body. It is preferably covered with an insulating sleeve and surrounded by a narrow gap so that the relative axial displaceability is ensured.

A preferred embodiment is characterised in that the coagulation electrodes are formed as two hook electrodes which extend at least substantially parallel to one another, with the cutting electrode being movably arranged between the hook electrodes. This embodiment is particularly expedient for engaging the tissue to be coagulated or cut.

In one embodiment the cutting electrode is secured to the proximal end of the conductive bar and is axially displaceable relative to the coagulation electrodes through the conductive bar which is displaceable by means of the actuating head. The cutting electrode can preferably be axially moved between the coagulation electrodes.

For the cutting process it is in this case particularly expedient to use an embodiment in which the cutting electrode is formed as a wire loop, in particular as a rhombic wire.

It is also possible to pivotally arrange the cutting electrode. A preferred embodiment of this kind is characterised in that the cutting electrode is pivotally arranged at the proximal end about a transverse axis and is drivable by the axially movable conductive bar to execute a pivotal cutting movement via a transmission which preferably comprises a pin and a cam-track. The cutting electrode can for example be pivotable in scissors-like manner from a position outside of the coagulation electrodes into a position between the coagulation electrodes.

Moreover, the cutting electrode is expediently formed as a wire hoop with a cutting part which can be brought between the coagulation electrodes, which is preferably at least approximately straight-lined or wave-shaped and which also extends in the inwardly pivoted state between the coagulation electrodes parallel to the latter. In this embodiment the wire hoop is conveniently arranged on a carrying arm which preferably extends parallel to the cutting part. Further advantageous developments of this embodiment can be found in claims 8 and 9.

Preferred embodiments of the actuating head are characterised in claims 10 to 16.

It is particularly advantageous when the shaft of the instrument is removable from the front end of the actuating head and moreover, when the stationary and movable parts of the actuating head are separable from one another. The individual parts can then each be conveniently cleaned on their own and can also if necessary, be sterilised.

Figure 6:
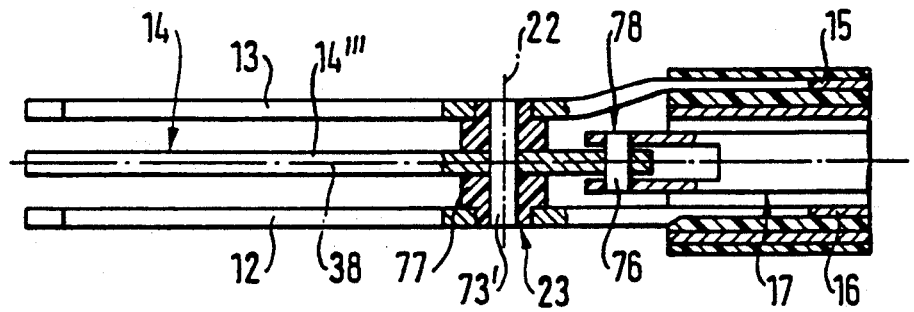

The invention will be described in the following with reference to the drawing in which are shown:

FIG. 1 a partly sectioned side view of the actuating head of the coagulation-cutting instrument of the invention, FIG. 2 a section on the line II—II in FIG. 1, FIG. 3 a twice broken away axial section through the instrument shaft of the coagulation-cutting instrument of the invention, FIG. 4 a sectional view of the front part of the instrument shaft of FIG. 3 turned through 90° about the axis of the instrument shaft relative to FIG. 3, FIG. 5 a sectional view analogous to FIG. 3 of the front part of the instrument shaft with a different embodiment of the cutting instrument, and FIG. 6 a view of the subject of FIG. 5 turned through 90° about the axis of the instrument shaft.

In accordance with FIGS. 3 and 4, an instrument shaft 11 having a constant circular cross section over the greatest part of its length has the following components disposed concentrically to the central axis 38 proceeding radially from the inside to the outside:

a conductive bar 17 covered with an insulating sleeve 34 and comprising a central rod 17' and a tube 17" firmly mounted on the latter and being extendible from the rest position shown in FIG. 3 in the direction of the arrow into a front end position illustrated in chain-dotted lines;

a gap 35 which permits the axial displacement of the conductive bar 17;

a conductive tube 16;

an insulating layer 36, a further conductive tube 15; and an outer insulating layer 37.

At the proximal end of the conductive bar 17, i.e. the end facing the patient, which in the rest position coincides essentially with the front end of the instrument shaft 11, there is provided a rhombus-shaped wire loop electrode which can be fed with a radio frequency current suitable for carrying out a cutting procedure. The front ends of the conductive tubes 15, 16 are, in accordance with FIG. 4, connected to a first fixed coagulation electrode 12 and to a second fixed coagulation electrode 13 respectively. In accordance with FIGS. 3 and 4, the two elongate and flat coagulation electrodes 12, 13 extend essentially parallel to the central axis 38 and form at their proximal ends a hook which is for example angled at right angles. In the rear region the coagulation electrodes 12, 13 are partly cylindrically formed in order to establish a continuous transition to the conductive tubes 15, 16 to which they are secured and with which they are electrically connected. The cutting electrode 14 extends symmetrically between the two coagulation electrodes 12, 13 and is displaceable by forward displacement of the conductive bar 17 out of the position shown in FIGS. 3 and 4 in full lines into the position reproduced in chain-dotted lines.

In the distal end region of the instrument shaft 11, a mounting flange 39 is provided in the external insulating layer 37 and behind it a ring seal 40. In this region a union or sleeve nut 41 is located on the instrument shaft 11 and is only schematically illustrated in chain-dotted lines in FIG. 3.

Behind the union nut 41 the different coaxial tubes terminate in stepped manner from the outside towards the inside with ever greater length so that the conductive tubes 15, 16 and also the central conductive bar 17 have greater parts of their peripheries exposed and can be brought in the manner which will be described in the following with respect to FIGS. 1 and 2, into a fixed mechanical and electrical connection with the actuating head 19.

It should be pointed out that the degree of projection of the individual coaxial elements is shown in FIG. 3 to a different scale from FIG. 1.

In accordance with FIG. 1, the distal end of the instrument shaft 11 is introduced into a central receiving bore 24 of the fixed part 20 of the actuating head 19. The fixed part 20 of the actuating head consists essentially of a plastic tube 42, with a preferably metallic end piece 43 attached to its front side, with the end piece having a central bore 44 in which a forwardly projecting threaded sleeve 45 is secured. The union nut 41 is axially screwed onto the external thread of the sleeve 45 and thereby presses the flange 39 against the front side of the threaded sleeve 45 via the seal 40. In this manner, the instrument shaft 11 is releasably secured to the actuating head 19.

Behind the insulating tube 42 there is arranged in axial alignment with it, a concentric (coaxial) contact sleeve 46 of insulating material which has eccentric bores 30, 47 extending parallel to the axis 38 at diametrically opposed positions, of which the upper bore is lined in accordance with FIG. 1 with a metallic sleeve 48 so that here a contact bore 30 is present.

Behind the insulating contact sleeve 46 and in axial alignment with the latter, there is provided a further insulating contact sleeve 49 secured to it which has bores 31, 50 axially aligned with the bores 30, 47. Only the bore 31 lying diametrically opposite to the upper bore 30 in FIG. 1 is again lined with a metal sleeve 51.

While the contact sleeve 46 has a central contact channel 25 for receiving the conductive tube 15, the contact sleeve 49 is provided with a central contact channel 26 of smaller diameter to receive the conductive tube 16.

Spring rings 52, 53 arranged in the wall of the contact sleeves 46, 49, ensure a conductive connection between the conductive tubes 15, 16 on the one hand, and the metal sleeves 48, 51 on the other hand.

The insulating tube 42 and the contact sleeves 46, 48 which are aligned therewith and which are connected axially together by means of the screws 54 which can be seen from FIG. 2, have a common cylindrical outer contour so that a metal guide sleeve 55 can be displaceably mounted thereon while being axially guided.

The guide sleeve 55 carries at its central region a clamping block 56 consisting of insulating material with a slotted central bore 57 through which the rear end of the conductive rod 17 or of the conductive bar 17' extends. The conductive bar 17 can be releasably secured in the clamping block 56, through a conical union nut 58 and pressure pins 59 which are axially fixed but radially displaceable relative to the guide sleeve 55 and which are connected with the clamping block 56. Thus, on the whole, a releasable mounting device 27 for the conductive bar 17 is present.

Electrically conductive contact pins 28, 29 are eccentrically fixedly arranged in the clamping block 56 and in alignment with the bores 30, 50 and 31, 47 respectively, with the contact pins 28, 29 engaging in a sliding seat into the bores 30, 50 and 31, 47 respectively.

In order to ensure adequate relative displacement of the head parts 20, 21, the bores preferably also extend in the illustrated manner into regions 60, 61 of the insulating tube 42.

The rear end of the conductive bar 17 contacts a contact pin 63 arranged in an insulating intermediate wall 62 which is connected via a line 64 with a connection coupling 18 provided at the end of the guide sleeve 55.

Two further cables 65, 66 lead, optionally via a capacitor 67, to the two contact pins 28, 29.

The front end plate 43 is pivotally connected via a screw 68 about a transverse axis to a resilient actuating grip 69, the other limb of which is connected via a screw 70 to a guide block 71 secured to the guide sleeve 55, with the guide block 71 being axially displaceably journalled on a guide bar 72 extending from the end plate 43 parallel to the axis 38.

The guide bar 72 is screwed into a corresponding threaded bore of the end plate 43 and a screw head 73 restricts the axial movement apart from one another of the guide sleeve 55 and also the insulating tube 42 brought about by the spring force of the grip 69.

The instrument can be dismantled in that, after screwing off the union nut 41 and releasing the union nut 58, the instrument shaft 11 is first extracted from the actuating head 19 The actuating handle 69 is then screwed away by releasing the screws 68, 70 and the guide rod 72 is removed by rotating it out by means of the screw head 73. The movable head part 21 can now be axially withdrawn from the fixed head part 20, with the contact pins 28, 29 being withdrawn axially out of the associated bores 30, 50, 60 and 31, 47, 61. All the necessary cleaning and repair work can now be carried out on the actuating head 19.

For the renewed assembly of the instrument, the two head parts 20, 21 are first put together with the actuating grip 69 to form the actuating head 19. The instrument shaft 11 shown in detail in FIGS. 3 and 4 is now inserted in the manner schematically illustrated in FIG. 1 with its distal end into the receiving bore 24 until the conductive bar 17 passes through the bore 57 and contacts the contact pin 63 and also the conductive tubes 15, 16 come into electrical contact with the conductive spring rings 52, 53. The instrument shaft 11 is then finally secured to the actuating head 19 by screwing the union nut 41 onto the threaded sleeve 45.

Through pressing together the resilient hand grip 69 the movable head part 21 is displaced in the direction of the fixed head part 20, with the conductive bar 17 being moved forwardly relative to the conductive tubes 15, 16 so that the rhombus-like cutting electrode 14, in accordance with FIGS. 3 and 4, is displaced out of the position shown in full lines into the front position illustrated in chain-dotted lines. The contact pins 28, 29 are thereby displaced in the contact bores 30, 31 while maintaining the electrical contact.

On relaxation of the resilient hand grip 69 the two heads 20, 21 move apart from one another again into the starting position which can be seen from FIGS. 1, 3 and 4.

In the retracted state, the cutting electrode 14, in accordance with FIGS. 3 and 4, lies between the coagulation electrodes which are bent around in partly cylindrical manner at the end. In this state, coagulations can be carried out with the instrument by applying a suitable radio frequency current to the coagulation electrodes 12, 13.

If a cutting process is to be carried out with the cutting electrode 14 then the surgeon actuates a non-illustrated changeover switch whereby a non-illustrated control device connects the two coagulation electrodes 12, 13 together to a single neutral electrode while the cutting electrode 14 is connected on actuation of a switch to a radio frequency current suitable for cutting. By means of the hook-like coagulation electrodes 12, 13, vessels or tissue elements can thus be cut with the cutting electrode 14

In accordance with FIGS. 5 and 6 in which the same reference numerals are used to designate components which have counterparts in the preceding figures, the cutting electrode 14 refers to a carrier arm 14''' which is pivotable about a transverse axis 22 with a wire hoop 14' being arranged on the carrier arm and extending in the downwardly pivoted state with a straight part 14'' between the two coagulation electrodes 12, 13. The part 14'' can also be made of wave-shape or of zigzag-shape. An arc-shape is also possible.

The bearing 23 for the transverse axle 22 comprises an insulating block 77 which contains a metal pin 73' which is arranged in the rear region of the coagulation electrodes 12, 13 and extends between them.

An actuating arm 74 of the cutting electrode 14 which extends behind the transverse axis 22 is provided with an elongate slot 75 which extends obliquely to the axis 38. A transverse pin 76 in the cam-track engagement extends into this elongate slot 75 and is secured to the front end of the conductive rod 17. The elongate slot 75 and the transverse pin 76 form a transmission 78 which converts a linear movement into a pivotal movement. By advancing the conductive bar 17 out of the position shown in solid lines in FIG. 5 a pivotal movement is thus produced for the cutting electrode 14 out of the position shown in continuous lines in FIG. 5 into the position reproduced in chain-dotted lines. Other suitable transmissions can also be used to generate a pivotal movement from a linear movement of the conductive bar 17.

The embodiment of FIGS. 5 and 6 operates during coagulation in the same manner as the embodiment of FIGS. 3 and 4, but in contrast operates in the following manner during cutting:

First of all, with the actuating grip 69 pressed (FIG. 1), i.e. in the open state of the cutting electrode 14 (chain-dotted illustration in FIG. 5) a vessel or tissue part is engaged by the hook-like coagulation electrodes 12, 13 which are in this case connected as a neutral electrode. As soon as this has taken place the high frequency cutting potential is applied to the cutting electrode 14, i.e. an arc is generated between the wire hoop 14' and the coagulation electrodes 12, 13, and the connective bar 17 is retracted, for example by release of the hand grip 69 of FIG. 1, with the wire hoop 14' pivoting between the coagulation electrodes 12, 13 and thereby cleanly cutting through the relevant tissue part.

I claim:

1. Medical radio frequency coagulation-cutting instrument comprising an instrument shaft (11) having a proximal end provided with first and second stationary coagulation electrodes (12, 13) and a movable cutting electrode (14); and an actuating head (19) arranged at a distal end of the instrument (11) and including a fixed head part (20) and a head part (21) which is movable relative thereto, wherein a relative movement of the two head parts (20, 21) is transmitted to the cutting electrode (14) wherein the coagulation electrodes (12, 13) and also the cutting electrode (14) lead via radio frequency supply lines (15, 16, 17), which are insulated relative to one another in the instrument shaft (11), to a cable connection (18) provided at the distal end for connection to a radio frequency supply device, and wherein the radio frequency supply device has at least two switch positions, in one of which the cutting electrode (14) is switched off and the coagulation electrodes (12, 13) are energized with a radio frequency coagulation current and in the other of which at least one of the coagulation electrodes (12, 13) is connected as a neutral electrode and a radio frequency voltage which enables a cutting arc is applied to the cutting electrode (14) and the neutral electrode, characterized in that the radio frequency supply lines for the first and second coagulation electrodes (12, 13) are conductive tubes (15, 16) arranged within one another, the radio frequency supply line for the cutting electrode (14) being arranged inside the conductive tubes in an insulated manner as an axially directed conductive bar (17) axially movable through the actuating head (19).

2. Instrument in accordance with claim 1, characterised in that the coagulation electrodes are formed as two hook electrodes (12, 13) which extend at least substantially parallel to one another, with the cutting electrode (14) being movably arranged between the hook electrodes.

3. Instrument in accordance with claim 1, characterised in that the cutting electrode (14) is secured to the proximal end of the conductive bar (17) and is axially displaceable relative to the coagulation electrodes (12, 13) through the conductive bar (17) which is displaceable by means of the actuating head (19).

4. Instrument in accordance with claim 1, characterised in that the cutting electrode (14) is formed as a wire loop, in particular of rhombic wire.

5. Instrument in accordance with claim 1, characterised in that the cutting electrode (14) is pivotally arranged at the proximal end about a transverse axis (22) and is drivable by the axially movable conductive bar (17) to execute a pivotal cutting movement via a transmission (78) which preferably comprises a pin (76) and a cam-track (75).

6. Instrument in accordance with claim 5, characterised in that the cutting electrode (14) is pivotable in scissors-like manner from a position outside of the coagulation electrodes (12, 13) into a position between the coagulation electrodes (12, 13).

7. Instrument in accordance with claim 5, characterised in that the cutting electrode (14) is formed as a wire hoop (14'), with a cutting part (14") which can be brought between the coagulation electrodes (12, 13), which is preferably at least approximately straight-lined or wave-shaped and which also extends in the inwardly pivoted state between the coagulation electrodes (12, 13) parallel to the latter.

8. Instrument in accordance with claim 7, characterised in that the wire hoop (14') is arranged on a carrying arm (14") which preferably extends parallel to the cutting part (14").

9. Instrument in accordance with claim 5, characterised in that an insulating bearing (23) extends between the coagulation electrodes (12, 13) in their rear region.

10. Instrument in accordance with claim 1, characterised in that the inner conductive tube (16) projects further rearwardly than the outer, conductive tube (15); and in that the fixed head part (20) of the actuating knob or handle (19) has a receiving bore (24) for the distal end of the instrument shaft (11) and behind this, has respective complimentary contact channels (25, 26) which are each aligned with one of the conductive tubes complementary to the latter, by means of which they are electrically connected to the cable connection (18).

11. Instrument in accordance with claim 10, characterised in that the conductive bar (17) projects rearwardly beyond the inner conductive tube (16); and in that a mounting device (27) for the rear end of the conductive bar (17) is provided in the movable head part (21) axially aligned with the contact channels (25, 26).

12. Instrument in accordance with claim 11, characterised in that the head parts (20, 21) are separable from one another; in that eccentrically arranged contact pins (28, 29) extend axially between the movable head part (21) and the stationary head part (20), are fixedly arranged in the one head part (21) and are axially slideably arranged in the other head part (20) in contact bores (30, 31); and in that the securing device (27) for the conductive bar (17) is releasable.

13. Instrument in accordance with claim 12, characterised in that the contact pins (28, 29) are eccentrically and fixedly arranged in an insulating block (32) which simultaneously forms a part of the securing device (27) for the conductive bar (17).

14. Instrument in accordance with claim 1, characterised in that the head parts (20, 21) are axially aligned with one another, essentially behind one another, and are preferably telescopically displaceable within one another.

15. Instrument in accordance with claim 1, characterised in that the head parts (20, 21) are separable from one another.

16. Instrument in accordance with claim 1, characterised in that an electrical plug connection (32) with at least three contacts is provided at the distal end of the movable head part (21).

* * * * *